US011562819B2

(12) United States Patent
Shantharam

(10) Patent No.: US 11,562,819 B2
(45) Date of Patent: Jan. 24, 2023

(54) METHOD AND SYSTEM FOR DETERMINING AND IMPROVING BEHAVIORAL INDEX

(71) Applicant: KAHA PTE. LTD., Singapore (SG)

(72) Inventor: Sudheendra Shantharam, Bengaluru (IN)

(73) Assignee: KAHA PTE. LTD., Singapore (SG)

( * ) Notice: Subject to any disclaimer, the term of this patent is extended or adjusted under 35 U.S.C. 154(b) by 144 days.

(21) Appl. No.: 16/978,586

(22) PCT Filed: Mar. 1, 2019

(86) PCT No.: PCT/SG2019/050118
§ 371 (c)(1),
(2) Date: Sep. 4, 2020

(87) PCT Pub. No.: WO2019/172843
PCT Pub. Date: Sep. 12, 2019

(65) Prior Publication Data
US 2021/0035675 A1 Feb. 4, 2021

(30) Foreign Application Priority Data
Mar. 5, 2018 (SG) .......................... 10201801749P

(51) Int. Cl.
G10L 15/26 (2006.01)
G10L 25/60 (2013.01)
G16H 20/70 (2018.01)
G10L 17/26 (2013.01)

(52) U.S. Cl.
CPC ............. *G16H 20/70* (2018.01); *G10L 15/26* (2013.01); *G10L 17/26* (2013.01); *G10L 25/60* (2013.01)

(58) Field of Classification Search
CPC ......... G10L 15/26; G10L 25/00; G10L 25/48; G10L 25/54; G10L 25/78; G10L 25/84; G10L 25/93
See application file for complete search history.

(56) References Cited

U.S. PATENT DOCUMENTS

| 10,339,957 | B1* | 7/2019 | Chenier | G10L 25/78 |
| 2008/0294439 | A1* | 11/2008 | Kirby | G10L 15/26 |
| | | | | 704/E15.045 |
| 2016/0220198 | A1* | 8/2016 | Proud | A61B 5/0022 |
| 2016/0363914 | A1 | 12/2016 | Kim et al. | |
| 2017/0140041 | A1* | 5/2017 | Dotan-Cohen | H04W 4/021 |
| 2018/0315441 | A1* | 11/2018 | Sapienza | G09B 19/04 |
| 2018/0366024 | A1* | 12/2018 | Yom-Tov | G16H 20/30 |
| 2019/0013010 | A1* | 1/2019 | Kokubo | G10L 15/187 |
| 2019/0189116 | A1* | 6/2019 | Li | G10L 15/07 |

FOREIGN PATENT DOCUMENTS

| CN | 106774861 A | 5/2017 | |
| JP | 2017-070804 A | 4/2017 | |
| WO | 2008/069187 A1 | 6/2008 | |
| WO | WO-2011122522 A1 * | 10/2011 | G10L 25/63 |

* cited by examiner

*Primary Examiner* — Paras D Shah
(74) *Attorney, Agent, or Firm* — Perilla Knox & Hildebrandt LLP; Kenneth A. Knox

(57) ABSTRACT

The present invention provides methods and systems determining the behavioural index of a user. The present invention involves analyzing the user's behaviour and linguistic parameters using a smart wearable device. Basis the analysis, user's behavioural index is suitably determined, modified and informed to the user.

9 Claims, 6 Drawing Sheets

(a)　　　　　　　　　　(b)

METHOD AND SYSTEM FOR DETERMINING AND IMPROVING BEHAVIORAL INDEX

FIELD OF THE INVENTION

The present invention relates generally to the field of analyzing user behaviour and in particularly relates to methods and systems for determining and improving behavioural index of user using a smart wearable device.

BACKGROUND OF THE INVENTION

Behaviour is a large component of how individuals communicate with each other. The behaviour varies from individual to individual. Thus, each individual communicates and reacts based on its respective behavioural nature. The behaviour nature of a person does not always remain the same and may change with the changing circumstances. For instance, an individual in stress may behave differently when not in stress. As a result of stressed circumstances, an individual may not behave properly and may reach differently to other individuals. The consequences of such improper or misbehaviour may have serious repercussions such as for example, social breakdown or even conflict with other individuals. In the past, many solutions have attempted to collect and gather information to aid individuals in understanding health, behaviour and various surrounding conditions. These systems have been limited in scope and capabilities, as they have not, among other things, adequately addressed the need to provide recommendations to change or improve the behaviour on a real time basis.

Accordingly, there exists a need to develop methods and systems that can analyze an individual's behaviour and assist them in improving their behavioural index.

SUMMARY OF THE INVENTION

In an embodiment, a method of determining the behavioural index of a user is provided. The method including the steps of: analyzing, using a smart device, one or more behaviour and linguistic parameters relating to said user; identifying count values corresponding to said more behaviour and linguistic parameters; comparing said count values with pre-defined threshold values corresponding to said more behaviour and linguistic parameters; and determining one or more of behaviour index, dignity index, linguistic index of user based on said comparison; providing said user with one or more recommendations based on said behaviour index.

It is an object of the invention to record resolutions taken by the users and recommend appropriate actions when said resolutions are not met and not properly followed by the user.

It is another object of the invention to recommend actions based on voice modulations of the user.

It is another object of the invention to suggest and correct pronunciation, modulation of the letter/word/sentence/syllable etc.

To further clarify advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF FIGURES

These and other features, aspects, and advantages of the present invention will become better understood when the following detailed description is read with reference to the accompanying drawings in which like characters represent like parts throughout the drawings, wherein.

Figure 1:
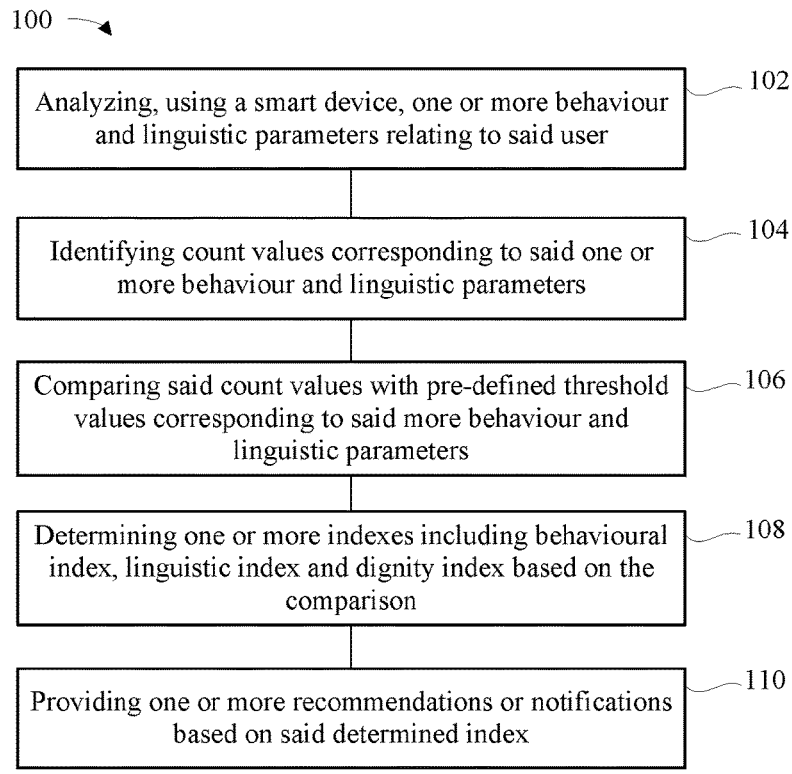
FIG. 1 shows a flowchart for a method of determining the behavioural index of a user in accordance with an embodiment of the present invention.

Further, skilled artisans will appreciate that elements in the drawings are illustrated for simplicity and may not have been necessarily been drawn to scale. For example, the flow charts illustrate the method in terms of the most prominent steps involved to help to improve understanding of aspects of the present invention. Furthermore, in terms of the construction of the device, one or more components of the device may have been represented in the drawings by conventional symbols, and the drawings may show only those specific details that are pertinent to understanding the embodiments of the present invention so as not to obscure the drawings with details that will be readily apparent to those of ordinary skill in the art having benefit of the description herein.

DETAILED DESCRIPTION

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

Reference throughout this specification to "an aspect", "another aspect" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Unless otherwise defined, all technical and scientific terms used herein have the same meaning as commonly understood by one of ordinary skill in the art to which this invention belongs. The system, methods, and examples provided herein are illustrative only and not intended to be limiting.

Embodiments of the present invention will be described below in detail with reference to the accompanying drawings.

FIG. 1 illustrates a flowchart for a method of determining the behavioural index of a user. The method 100 includes step 102 of analyzing, using a smart device, one or more behaviour and linguistic parameters relating to said user. The smart device is generally a smart wearable device, including but not limited, to a smart watch, smart fitness bands, smart shoes, smart glass, smart earphones/headphones, smart clothing, smart jewellery to name a few. The smart device is configured to operationally interconnect to a mobile device. The behavioural parameters include, but not limited to, clear signs of distress, erratic behaviour, threatening words or actions, violent or aggressive behaviour, classroom disruptions, lack of responsiveness, lack of expression, relationship violence, alienation/isolation from others, words that convey clear intentions to harm oneself or others, or attempt suicide, including threats, gestures, ideations, and attempts, observing self-injurious behaviour (such as cutting or burning), extreme rudeness or insubordination towards people (known or unknown), Extreme or sudden changes in behaviour, facial expressions, action tendencies etc. The linguistic parameters include, but not limited to, language, formal & informal use of language, grammar, flow of words, bad words, word resolutions level of vocabulary, use of different languages, depth of language etc. The method 100 further includes step 104 of identifying count values corresponding to said one or more behaviour and linguistic parameters and step 106 of comparing said count values with pre-defined threshold values corresponding to said one or more behaviour and linguistic parameters. The threshold values are pre-defined and may be updated from time to time. The threshold values may vary from user to user. Based on the comparison, one or more indexes including behavioural, linguistic index and dignity index is determined in step 108 and the user is provided with one or more recommendations or notifications based on said determined behaviour index in step 110.

In an embodiment, the method 100 includes recording one or more resolutions/decisions taken by users and the system will take appropriate actions when such resolutions are not properly followed by the user. Further, any compromise to such resolution/decisions are detected by the system, then the system appropriately send notifications, alerts, warnings, indications to the user through vibration, visual indication, sound, voice etc.

In an embodiment, the method 100 includes creating, modifying and determining the dignity index corresponding to a user. The analysis involves monitoring the nature of words spoken by the user, language used by the user, decibel value of the user and so on. Based on the analysis, the dignity index may be suitably modified. In another embodiment, the method 100 also includes monitoring voice modulations of the user.

In another embodiment, the method 100 further includes a pronunciation module (for suggestion of words, and correcting pronunciation, modulation of the letter/word/sentence/syllable etc). The method 100 is configured to record and provide a language summary for a specific time period (day/week/month/year etc).

Figure 2:
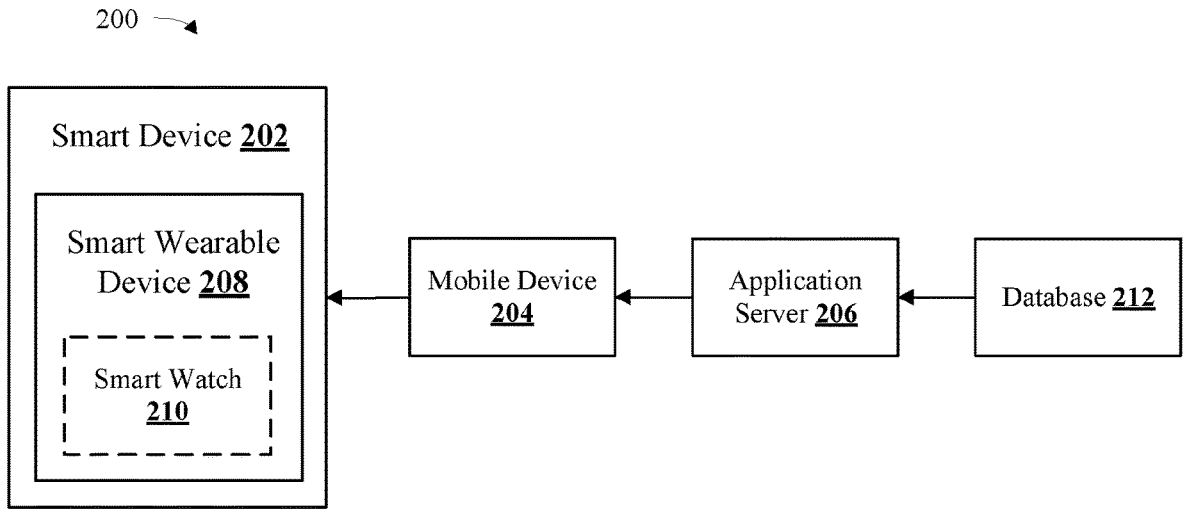
FIG. 2 shows a block diagram of the broad level system for determining the behavioural index of a user in accordance with an embodiment of the present invention.

Referring to FIG. 2, a block diagram of the broad level system for determining the behavioural index of a user is provided. The system 200 includes a smart device 202 connected to a mobile device 204, an application server 206 and a database 212. The smart device 202 preferably includes a smart wearable device 208. The smart wearable device 208, including but not limited, to a smart watch 210, smart fitness bands, smart shoes, smart glass, smart earphones/headphones, smart clothing, smart jewellery to name a few. The mobile device 204 is configured with an application which is capable of monitoring, recording, and analyzing the user data. The quantify values corresponding to the behaviour, linguistic, resolution parameters are monitored using the smart device 202 and mobile device 204 and transmitted to the application server 206. The application server 206 processes and compares the subject real-time values with threshold values, recommends and notifies the user based on such processing of values. The database 212 stores all the details pertaining to various activities of the user required for determining the quantify values corresponding to the behaviour, linguistic, resolution parameters, along with the set of threshold values for each behaviour, linguistic pattern and resolution. The database 212 may contain dictionary (specific for every language, including way of speaking, slang, etc), grammatical data of language, multi-linguistic dictionaries, conversational words etc. In an embodiment, the database 210 may auto-catalogue words/letters/sentences depending on the requirement. In an embodiment, the database maintains plurality of sub-data units to store different set of information relating linguistic, verbal, vocal communication. The system 200 is primarily configured to analyze the behaviour of the user (through voice variation, modulation etc) in real-time and notify (alert) the user, when the pre-set configuration/conditions (threshold values) do not match.

Figure 3:
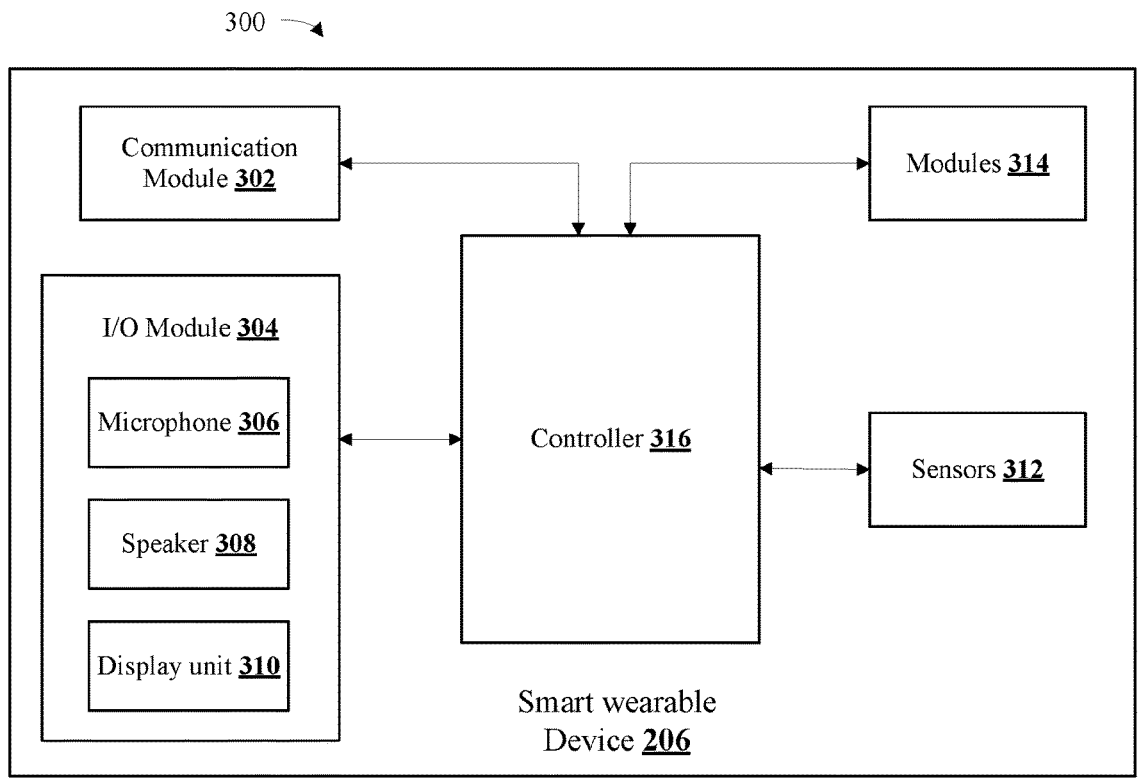
FIG. 3 shows a block diagram of the smart wearable device as referred in FIG. 2 in accordance with an embodiment of the present invention.

Referring to FIG. 3, a block diagram of the smart wearable device as referred in FIG. 2 in accordance with an embodiment of the present invention is provided. The smart wearable device 206 includes a communication module 302 that is configured to operationally interconnect with the mobile device 204 and application server 206. The communication module 302 is responsible for communicating, transferring and receiving data from the mobile device 204 and application server 206. The smart wearable device 206 further includes an I/O module 304 that comprise a microphone 306, speaker 308 and a display unit 310. The microphone 306 is configured to record the voice of the user. The speaker 308 outputs the activities, instructions, codewords etc. The display unit 310 shows the notifications, updates or any activity related information, received from sensors 312, modules 314 or any information received from the mobile device 204. The smart wearable modules 314 are configured to analyze the behaviour, language of the user, decibel value of the words spoken by the user. The sensors 312 may be configured for recording the activities, voice variations of the user. The sensors 312 may include, but not limited to accelerometer, gyroscope, sound sensor etc. The smart wearable device 206 further includes a processing Controller 316 that is configured to analyze and process details of various activities and communicate the same to other modules of the system 300.

Figure 4:
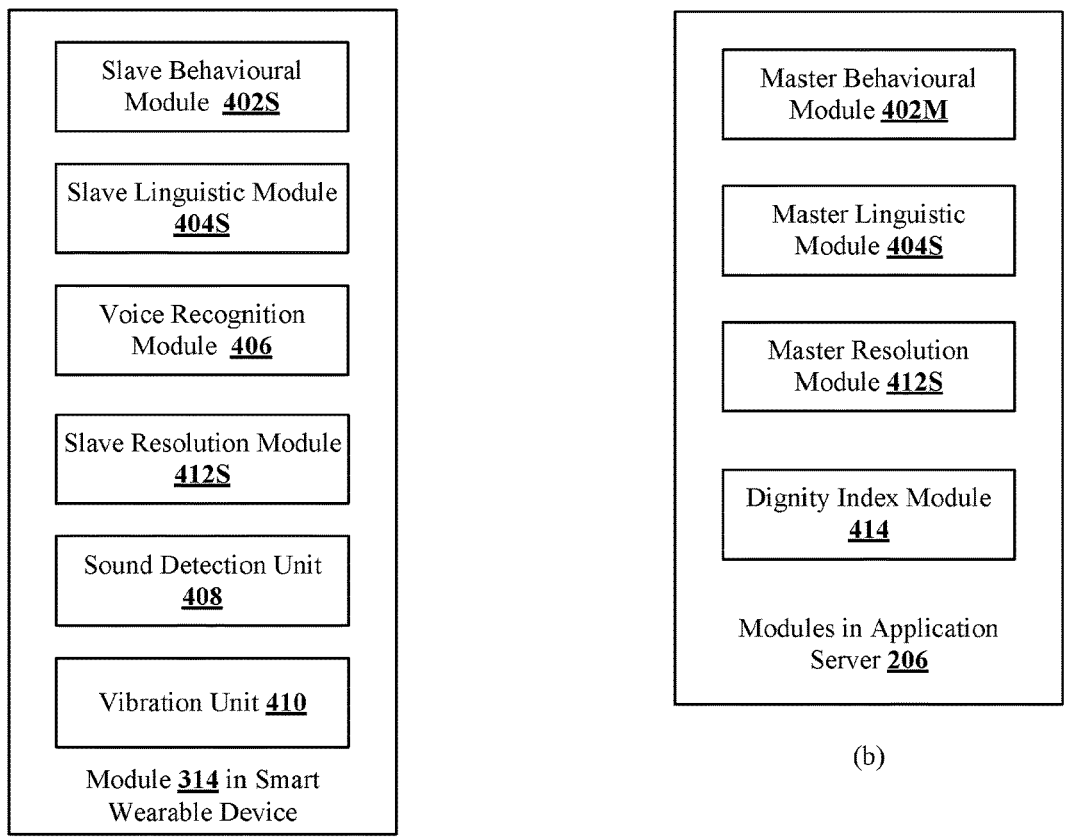
FIG. 4(a)-(b) show a block diagram of the modules of the smart wearable device and application server respectively in accordance with an embodiment of the present invention.

Referring to FIG. 4a, a block diagram of the modules of the smart wearable device as referred in FIG. 3 in accordance with an embodiment of the present invention is provided. The module 314 includes a slave behavioural module 402S that is configured to detect behavioural parameters of the user. The behavioural parameters include, but not limited to, clear signs of distress, erratic behaviour, threatening words or actions, violent or aggressive behaviour, classroom disruptions, lack of responsiveness, lack of expression, relationship violence, alienation/isolation from others, words that convey clear intentions to harm oneself or others, attempt to suicide, including threats, gestures, ideations, and attempts, observing self-injurious behaviour (such as cutting or burning), extreme rudeness or insubordination towards people (known or unknown), Extreme or sudden changes in behaviour, facial expressions, action tendencies etc.

A slave linguistic module 404S is further provided for detecting and analyzing the linguistic parameters. The linguistic parameters include but not limited to language, formal & informal use of language, grammar, flow of words, bad words, level of vocabulary, use of different languages, depth of language etc. The module 314 also includes a voice recognition module 406 that is capable of analyzing the voice modulation of the user and hence detecting the voice parameters of the user. A sound detection unit 408 is provided to record various sounds in the environment apart from voice and works with voice recognition module, to efficiently detect the voice and modulation. A vibration unit 410 is provided for sensing the variations through the smart wearable device. In an embodiment, the recorded voice of a user is processed by the voice recognition module (microphone) 406 and split/charted with decibel index. A decibel scale is created with respect to the existing decibel values (for each word, sentence, syllable stored in the database).

The module 314 also includes a slave resolution module 412S that is configured to record the resolutions taken by the users. The users can feed any number of decisions/resolutions, which they would like to do and get the motivation. Any compromise to such resolutions/decisions is detected and appropriately notifications are sent to the user through vibration, visual indication, sound etc. For example, the resolution given by user may be "I will not talk bad words", the system upon receiving, analyzes the content and appropriately creates a catalogue of appropriate words (all bad words in this case) not to be pronounced by the user.

The slave behavioural module 402S, slave linguistic module 404S, voice recognition module 406, slave resolution module 412S are configured to analyze individual decibel values and determine the decibel scale. The various modules are mapped appropriately with the modules of application server 206 as referred in FIG. 4b. The modules of the application server are referred to as primary modules and include a master behavioural module 402M, master linguistic module 404M, master resolution module 412M. Each of the aforesaid modules is suitably mapped with the slave modules of the smart wearable device. The details (values) monitored by the respective modules of the smart wearable device are compared with the threshold values by the respective modules of the application server and accordingly appropriate notifications are created and alerts are sent to the user. The application server 206 also includes dignity index module 414 that is configured to maintain a dignity index with a credit value (for example a "Dignity credit", if user speaks good words/pronunciation etc, the dignity credit will increase) for every word, sentence etc. When the user speaks such word, then the system immediately responds with a message saying "Bad word is detected, you sworn earlier not to use this word at any cost", and "Your dignity credit reduces if you continuously use this word". The system eventually keeps the user alert about his speaking. The system may incorporate a machine learning algorithm which continuously absorbs and understands nature of various types of human interactions, in real-time. In an embodiment, the algorithm maintains different rules but not limited to grammar, behaviour, activity etc. These rules are pre-programmed and appropriately updated in time to time. The analysis to determine the desired behavioural or linguistic or resolution index takes place at both the slave and master modules. In another embodiment, the modules in smart wearable 208 are secondary modules and that of application server 206 are primary modules.

Referring to FIG. 5 to FIG. 8, flow charts for determining and adjusting the dignity index of a user in accordance with an exemplary embodiment of the invention are provided. In the exemplary implementations, the dignity index is determined and adjusted by monitoring and analyzing the voice and language spoken by the user. The linguistic module as described previously is primarily involved in determining the dignity index based on the words used by the user while speaking.

Figure 5:
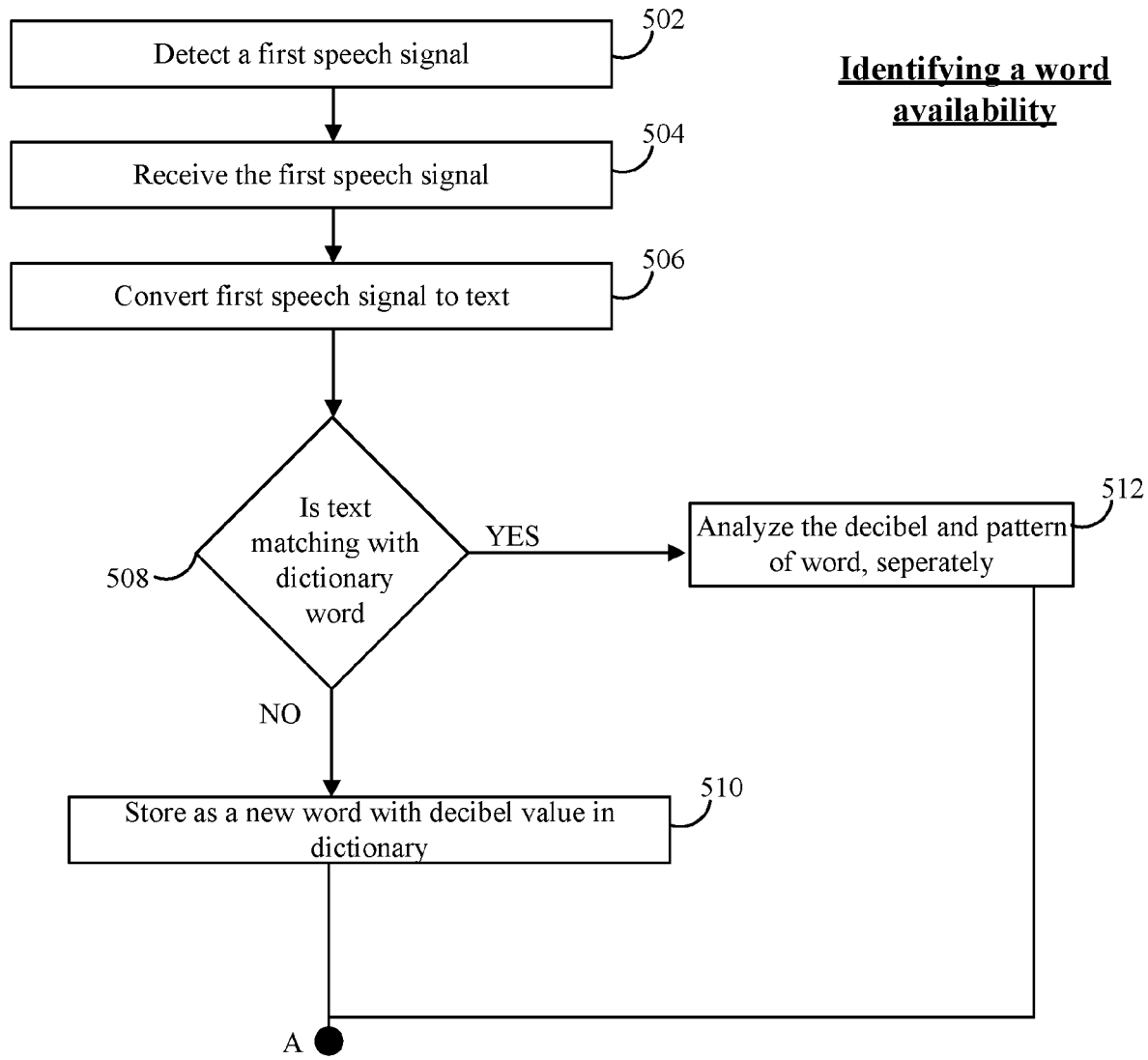
FIG. 5 shows a flow chart for identifying availability of the word as spoken by the user in accordance with an exemplary embodiment of the present invention.

Referring to FIG. 5, a flow chart for identifying availability of the word as spoken by the user is illustrated. The flow chart begins at block 502 wherein the first speech signal is detected and received at block 504. The received speech signal is converted into text using suitable speech to text converters in block 506. Once the speech to text process is completed and detected by the system, it is ascertained if the text matches with a pre-stored dictionary word in block 508. If No match is detected in block 508, the text is stored with the decibel value as a new word in the dictionary as indicated in block 510. If a match is detected in block 508, the decibel value of the word text and the pattern of the word text are analyzed separately as indicated in block 512.

Figure 6:
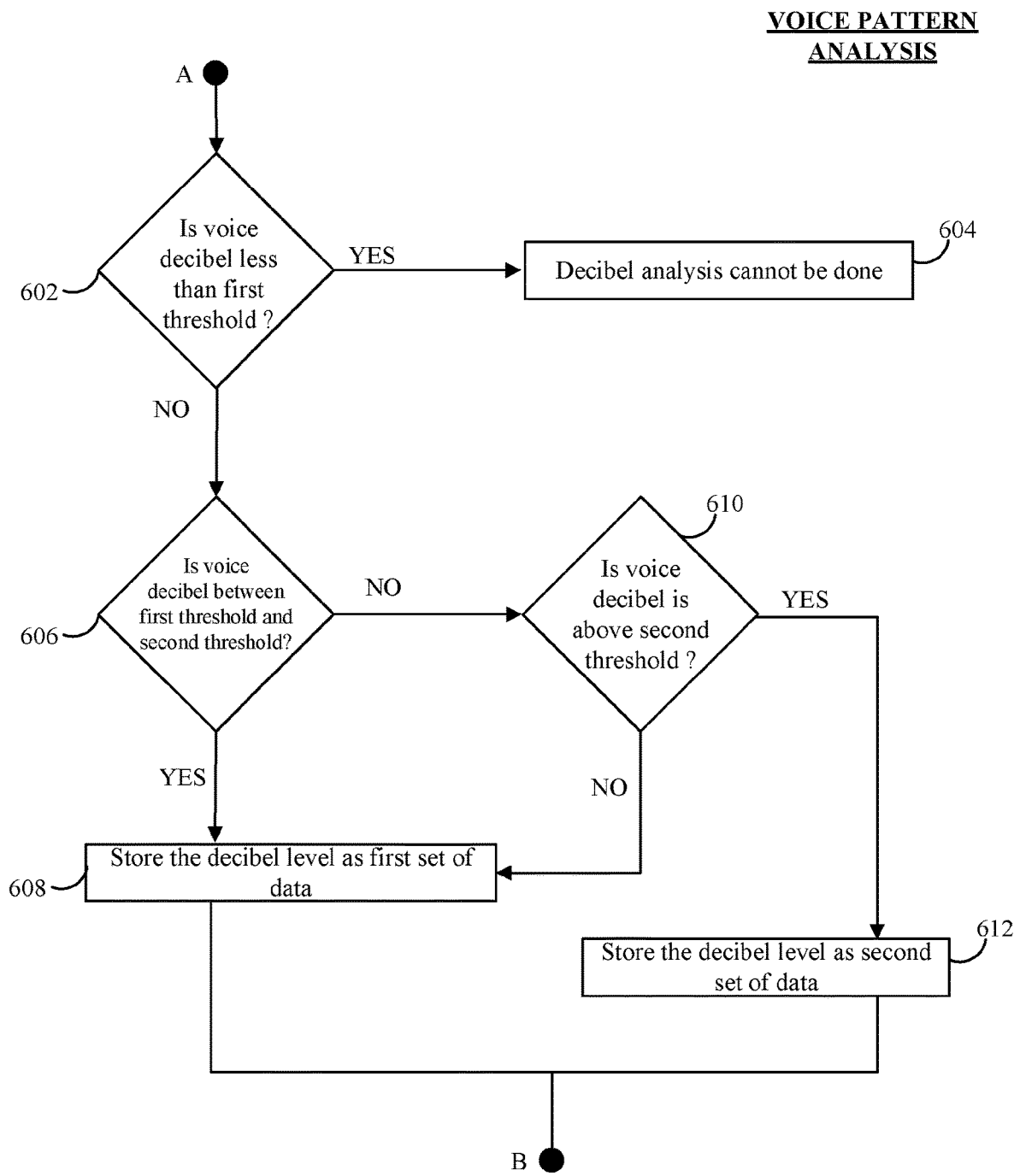
FIG. 6 shows a flow chart for analyzing the voice pattern of the speech signal as spoken by the user in accordance with an exemplary embodiment of the present invention.

Referring to FIG. 6, a flow chart for analyzing the voice pattern of the speech signal as spoken by the user is illustrated. The flow chart is illustrated to analyze the decibel level of the word text referred in block 512 in FIG. 5. At block 602, the decibel level is matched with a first pre-stored threshold level. In case the decibel level is less than the first-threshold level, an error is set to the user that the decibel analysis cannot be done in block 604. In case the decibel level is higher than the first-threshold level based on the matching done in block 602, a comparison is performed to determine if the decibel level is between pre-defined first threshold level and pre-defined second threshold level in block 606. Considering the comparison, if it is determined that the decibel level is between the pre-defined first and second threshold level, the decibel level is stored as first set of data in block 608 and if it is determined that the decibel level is above the pre-defined second threshold level at block 610, the decibel level is stored as second set of data in block 612.

Figure 7:
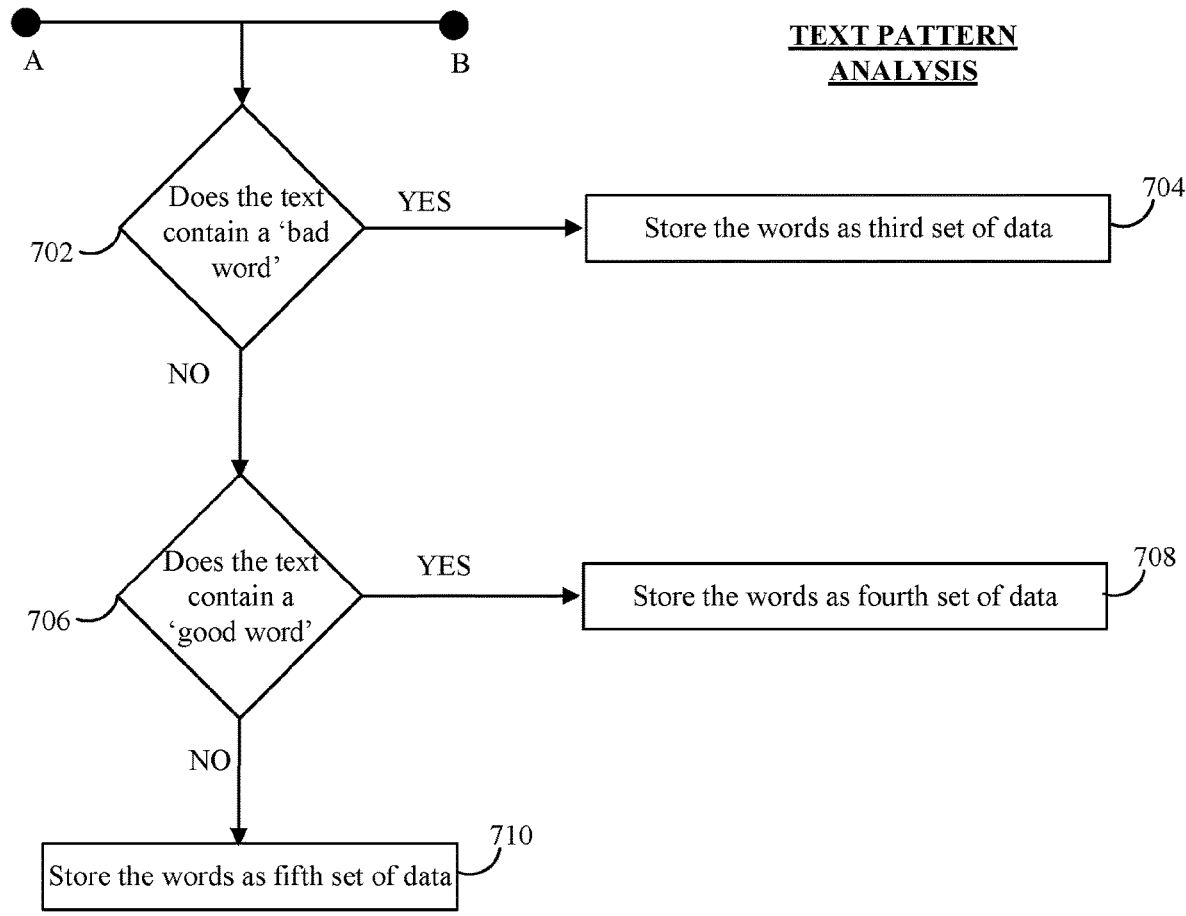
FIG. 7 shows a flow chart for analyzing the text pattern in accordance with an exemplary embodiment of the present invention.

Referring to FIG. 7, a flow chart for analyzing the text pattern is illustrated. The flow chart is illustrated to analyze the pattern of the word text referred in block 512 in FIG. 5. At block 702, the text pattern is analyzed, if it contains a pre-defined word categorized as a bad word. If the analysis indicates that the text pattern contains a bad word, the words are stored as third set of data in block 704. In the alternative, if the analysis indicates that the text pattern contains a pre-defined good word in block 706, the words are stored as fourth set of data in block 708. In case the text does not contain a good word (or may be a neutral word) in block 708, the words are stored as fifth set of data in block 710.

Figure 8:
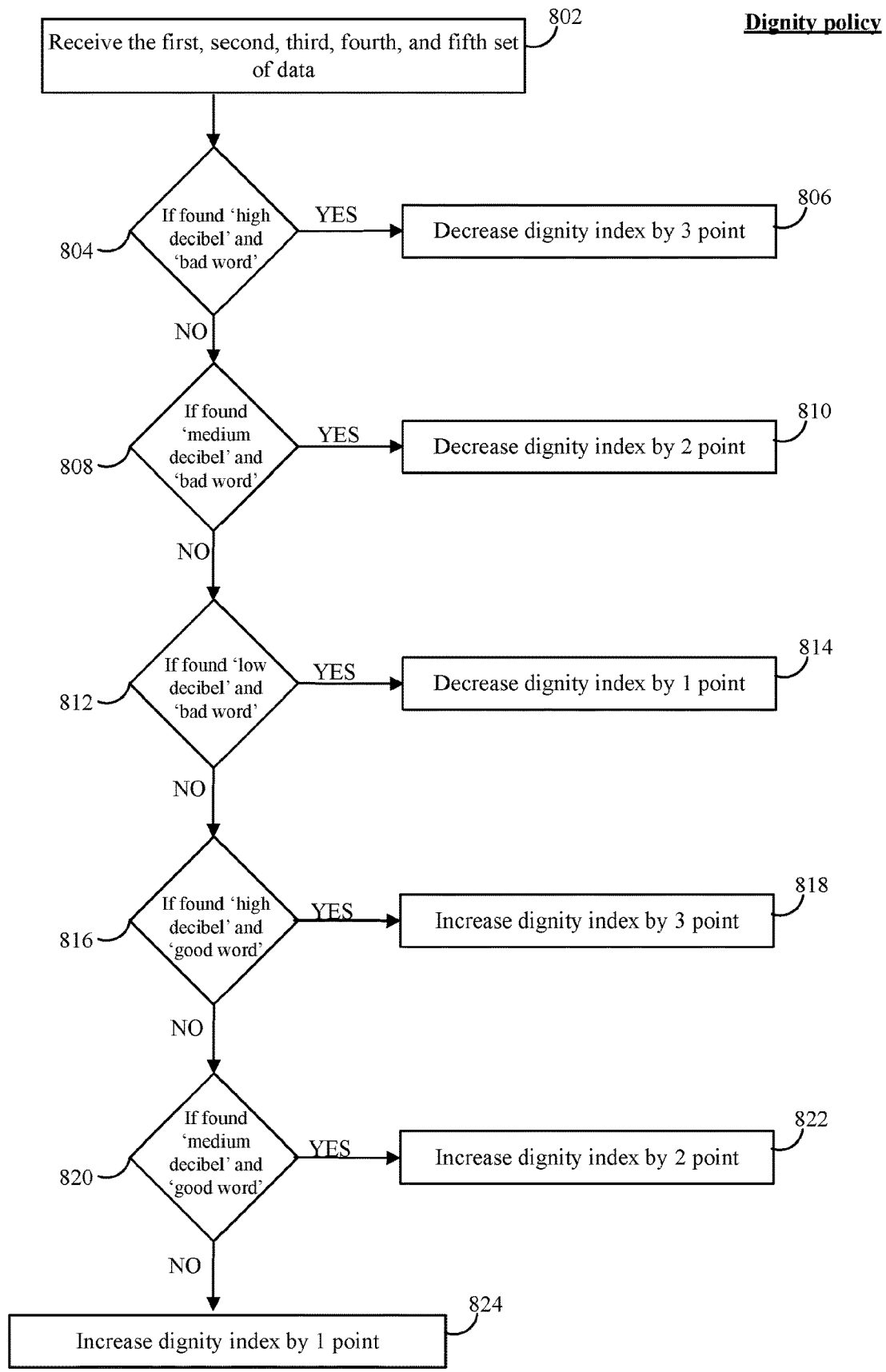
FIG. 8 shows a flow chart for illustrating the dignity policy in accordance with an exemplary embodiment of the invention.

Referring to FIG. 8, a flow chart for illustrating the dignity policy in accordance with an exemplary embodiment of the invention is illustrated. The dignity policy is defined to adjust the dignity index of the user. Reference may be made to FIGS. 5-7 for the purposes of explanation of FIG. 8. The flow chart begins with receiving of first, second, third, fourth, and fifth set of data (as derived in FIGS. 6 and FIGS. 7) in block 802. Based on the analysis in respect of the first, second, third, fourth, and fifth set of data, the dignity index is suitably determined, modified and adjusted. If the decibel level is found to be of 'high' level (more than a threshold level set by the system) and the text pattern is found to contain a 'bad word' in block 804, the dignity index is decreased by 3 points as shown in block 806. If the decibel level is found to be of 'medium' level and the text pattern is found to contain a 'bad word' in block 808, the dignity index is decreased by 2 points as shown in block 810. If the decibel level is found to be of 'low' level and the text pattern is found to contain a 'bad word' in block 812, the dignity index is decreased by 1 point as shown in block 814. If the decibel level is found to be of 'high' level and the text pattern is found to contain a 'good word' in block 816, the dignity index is increased by 3 points as shown in block 818. If the decibel level is found to be of 'medium' level and the text pattern is found to contain a 'good word' in block 820, the dignity index is increased by 2 points as shown in block 822; else the dignity index is increased by 1 point as shown in block 824. Thus, it can be noticed that the dignity index is varied based on the decibel value and the nature of words spoken by the user. In an embodiment, an instant notification and alert is sent to the user (preferably, to a smart wearable device), whenever the user speaks any bad word and the same is detected by the system. In an embodiment, the dignity index may be varied based on the number of good or bad words spoken by the user. The list of good words and bad words are pre-defined by the user or system and may be updated from time to time.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. Benefits, other advantages, and solutions to problems have been described above with regard to specific embodiments.

I claim:
1. A method for improving behavior of a user of a smart device, comprising:
analyzing, using the smart device, a plurality of behavior and linguistic parameters relating to the user;
identifying count values corresponding to the plurality of behavior and linguistic parameters;
comparing the count values with pre-defined threshold values corresponding to the plurality of behavior and linguistic parameters;
determining a behavior index, a dignity index, and a linguistic index of the user based on said comparison;
generating and sending a communication to provide the user with at least one recommendation based on the behavior index, the dignity index, and the linguistic index;
in response to the communication with the at least one recommendation being provided to the user, modifying the behavior index, the dignity index, and the linguistic index of the user, wherein the dignity index is modified based at least in part by:
detecting a speech signal of the user;
converting the speech signal into text comprising a plurality of words;
computing a decibel level corresponding with the speech signal;
selecting at least one word from the plurality of words to estimate presence of the at least one word within a dictionary comprising a plurality of pre-stored words;
storing the at least one word and the corresponding decibel level as a new word within the dictionary when the at least one word is not found within the dictionary, wherein the dictionary is a personal dictionary of the user;
classifying the decibel level into at least one category of a decibel classification, wherein the at least one category of the decibel classification has a corresponding range of decibel values, by:
classifying the decibel level into a low category when the computed decibel level is lower than a first threshold decibel value;
classifying the decibel level into a medium category when the computed decibel level is within a range of the first threshold decibel value and a second threshold decibel value; and
classifying the decibel level into a high category when the decibel level is greater than the second threshold decibel value;
classifying the at least one word into at least one of a first list of words and a second list of words, wherein the first list of words includes pre-stored prohibited words for the user and the second list of words includes pre-stored non-prohibited words for the user;
computing an extent of modification required in the dignity index of the user in accordance with the classification of the decibel level into at least one category of the decibel classification and the classification of the at least one word into at least one of the first list and the second list of words;

decreasing the dignity index by at least three points when the decibel level is within the high category and when the least one word is classified in the first list of words;

decreasing the dignity index by at least two points when the decibel level is within the medium category and when the least one word is classified in the first list of words; and decreasing the dignity index by at least one point when the decibel level is within the low category and when the least one word is classified in the first list of words;

recording a plurality of resolutions undertaken by the user in response to the communication with the at least one recommendation being provided to the user;

detecting a compromise made by the user to at least one resolution among the plurality of resolutions; and notifying the user regarding the detected compromise by directing a vibration device to vibrate to notify the user regarding the detected compromise.

2. The method as claimed in claim 1, further comprising:
alerting the user about non-analysis of the speech signal when the computed decibel level is below a minimum threshold level required for analyzing the computed decibel level.

3. The method as claimed in claim 1, further comprising:
increasing the dignity index by at least three points when the decibel level is within the high category and when the least one word is classified in the second list of words;

increasing the dignity index by at least two points when the decibel level is within the medium category and when the least one word is classified in the second list of words; and increasing the dignity index by at least one point when the decibel level is within the low category and when the least one word is classified in the second list of words.

4. The method as claimed in claim 1, further comprising:
recommending pronunciation and speech modulation of the at least one word to the user.

5. A system for improving behavior, comprising:
a smart device comprising at least one hardware processor, and program instructions stored in memory and executable in the smart device that, when executed, direct the smart device to:
analyze a plurality of behavior and linguistic parameters relating to a user of the smart device;
identify count values corresponding to the plurality of behavior parameters and identify count values corresponding to the plurality of linguistic parameters;
perform a comparison of the count values with predefined threshold values corresponding to the plurality of behavior and linguistic parameters;
determine a behavior index, a dignity index, and a linguistic index of the user based on the comparison;
generate and send a communication to provide the user with at least one recommendation based on the behavior index, the dignity index, and the linguistic index;
in response to the communication with the at least one recommendation being provided to the user, modify the behavior index, the dignity index, and the linguistic index of the user, wherein the dignity index is modified based at least in part by:

detecting a speech signal of the user, convert the speech signal into text comprising a plurality of words, and compute a decibel level corresponding with the speech signal;
selecting at least one word from the plurality of words to estimate presence of the at least one word within a dictionary comprising a plurality of pre-stored words;
storing the at least one word and the corresponding decibel level as a new word within the dictionary when the at least one word is not found within the dictionary, wherein the dictionary is a personal dictionary of the user;
classifying the decibel level into at least one category of a decibel classification, wherein the at least one category of the decibel classification has a corresponding range of decibel values, by:
classifying the decibel level into a low category when the computed decibel level is lower than a first threshold decibel value;
classifying the decibel level into a medium category when the computed decibel level is within a range of the first threshold decibel value and a second threshold decibel value; and
classifying the decibel level into a high category when the decibel level is greater than the second threshold decibel value;
classifying the at least one word into at least one of a first list of words and a second list of words, wherein the first list of words includes pre-stored prohibited words for the user and the second list of words includes pre-stored non-prohibited words for the user;
computing an extent of modification required in the dignity index of the user in accordance with the classification of the decibel level into at least one category of the decibel classification and the classification of the at least one word into at least one of the first list and the second list of words;
decreasing the dignity index by at least three points when the decibel level is within the high category and when the least one word is classified in the first list of words;
decreasing the dignity index by at least two points when the decibel level is within the medium category and when the least one word is classified in the first list of words; and
decreasing the dignity index by at least one point when the decibel level is within the low category and when the least one word is classified in the first list of words;
record a plurality of resolutions undertaken by the user in response to the communication with the at least one recommendation being provided to the user;
detect a compromise made by the user to at least one resolution among the plurality of resolutions; and
notify the user regarding the detected compromise to the user; and
a vibration device configured to vibrate to notify the user regarding the detected compromise to the user.

6. A method for improving behavior of a user of a smart device, comprising:
analyzing, using the smart device, a plurality of behavior and linguistic parameters relating to the user;
identifying count values corresponding to the plurality of behavior and linguistic parameters;

performing a comparison of the count values with predefined threshold values corresponding to the plurality of behavior and linguistic parameters;

determining of a behavior index, a dignity index, and a linguistic index of the user based on the comparison;

providing the user with at least one recommendation based on the the behavior index, the dignity index, and the linguistic index;

in response to the communication with the at least one recommendation being provided to the user, modifying the behavior index, the dignity index, and the linguistic index of the user, wherein the dignity index is modified based at least in part by:

detecting a speech signal of the user;

converting the speech signal into text comprising a plurality of words; and computing a decibel level corresponding with the speech signal;

selecting at least one word from the plurality of words to estimate presence of the at least one word within a dictionary comprising a plurality of pre-stored words;

storing the at least one word and the corresponding decibel level as a new word within the dictionary when the at least one word is not found within the dictionary, wherein the dictionary is a personal dictionary of the user;

classifying the decibel level into at least one category of a decibel classification, wherein the at least one category of the decibel classification has a corresponding range of decibel values, by:

classifying the decibel level into a low category when the computed decibel level is lower than a first threshold decibel value;

classifying the decibel level into a medium category when the computed decibel level is within a range of the first threshold decibel value and a second threshold decibel value; and classifying the decibel level into a high category when the decibel level is greater than the second threshold decibel value;

classifying the at least one word into at least one of a first list and a second list of words, wherein the first list of words includes pre-stored prohibited words for the user and the second list of words includes pre-stored non-prohibited words for the user;

computing an extent of modification required in the dignity index of the user in accordance with the classification of the decibel level into at least one category of the decibel classification and the classification of the at least one word into at least one of the first list and the second list of words;

increasing the dignity index by at least three points when the decibel level is within the high category and when the least one word is classified in the second list of words;

increasing the dignity index by at least two points when the decibel level is within the medium category and when the least one word is classified in the second list of words; and increasing the dignity index by at least one point when the decibel level is within the low category and when the least one word is classified in the second list of words;

recording a plurality of resolutions undertaken by the user in response to the communication with the at least one recommendation being provided to the user;

detecting a compromise made by the user to at least one resolution among the plurality of resolutions; and notifying the user regarding the detected compromise by directing a vibration device to vibrate to notify the user regarding the detected compromise.

7. The method according to claim 6, generating and communicating an alert to the user regarding non-analysis of the speech signal when the computed decibel level is below a minimum threshold level required for analyzing the computed decibel level.

8. The method according to claim 6, further comprising:

decreasing the dignity index by at least three points when the decibel level is within the high category and when the least one word is classified in the first list of words;

decreasing the dignity index by at least two points when the decibel level is within the medium category and when the least one word is classified in the first list of words; and decreasing the dignity index by at least one point when the decibel level is within the low category and when the least one word is classified in the first list of words.

9. The method according to claim 6, further comprising generating and sending a communication that recommends pronunciation and speech modulation of the at least one word to the user.

* * * * *